United States Patent
Kumar et al.

(10) Patent No.: US 6,983,749 B2
(45) Date of Patent: Jan. 10, 2006

(54) INDUCING HYPOTHERMIA AND REWARMING USING A HELIUM-OXYGEN MIXTURE

(75) Inventors: Matthew M. Kumar, Oronoco, MN (US); Larry D. Johnson, Hastings, MN (US)

(73) Assignee: Minnesota High-Tech Resources, LLC, Red Wing, MN (US)

( * ) Notice: Subject to any disclaimer, the term of this patent is extended or adjusted under 35 U.S.C. 154(b) by 200 days.

(21) Appl. No.: 10/310,118

(22) Filed: Dec. 4, 2002

(65) Prior Publication Data

US 2003/0131844 A1    Jul. 17, 2003

Related U.S. Application Data

(60) Provisional application No. 60/405,137, filed on Aug. 22, 2002, provisional application No. 60/377,335, filed on Apr. 30, 2002, provisional application No. 60/336,668, filed on Dec. 4, 2001.

(51) Int. Cl.
*A61M 16/00* (2006.01)
*A62B 7/00* (2006.01)
*F24F 5/00* (2006.01)

(52) U.S. Cl. ............................ 128/204.15; 128/200.14; 128/204.18; 128/913

(58) Field of Classification Search ............ 128/200.14, 128/200.21, 203.12, 203.16, 203.17, 203.26, 128/204.14, 204.15, 204.17, 204.18, 913, 128/201.13, 207.14; 61/1
See application file for complete search history.

(56) References Cited

U.S. PATENT DOCUMENTS

| | | | | |
|---|---|---|---|---|
| 5,335,650 A | * | 8/1994 | Shaffer et al. ......... | 128/200.24 |
| 5,429,123 A | * | 7/1995 | Shaffer et al. ......... | 128/204.23 |
| 5,540,225 A | * | 7/1996 | Schutt .................... | 128/207.15 |
| 5,706,830 A | * | 1/1998 | Parker .................... | 128/203.12 |
| 6,041,777 A | * | 3/2000 | Faithfull et al. ....... | 128/200.24 |
| 6,131,571 A | | 10/2000 | Lampotang et al. ... | 128/204.21 |
| 6,166,092 A | | 12/2000 | Sekins et al. ............... | 514/772 |
| 6,244,052 B1 | | 6/2001 | Kasza ............................. | 62/1 |

(Continued)

FOREIGN PATENT DOCUMENTS

WO    WO 95/16484    6/1995

(Continued)

OTHER PUBLICATIONS

Platt, Charles, "Future Tech: Here Breathe This Liquid," DISCOVER, vol. 22, No. 10 (2001).

(Continued)

*Primary Examiner*—Henry Bennett
*Assistant Examiner*—Amanda Wieker
(74) *Attorney, Agent, or Firm*—Craig Taylor Law Office, PLLC

(57) ABSTRACT

Devices and methods to heat and cool human beings, including inducing and maintaining hypothermia in human patients. Methods include inducing hypothermia to treat ischemic events, including heart attack and stroke, to limit damage caused by the ischemic event. Methods can include: using the lungs for heat exchange; using cooled gases for ventilation; using helium in the ventilation gas mixture, using medications to control reflex heat production; and injecting a perfluorocarbon mist into the gas stream to increase the cooling rate. The high thermal conductivity and diffusivity of helium results in greater inspired gas temperature equalization toward body temperature. Due to the latent heat of vaporization, addition of even small quantity of phase-change perfluorocarbon dramatically increases the heat carrying capacity of the respiratory gases. Hypothermia may be terminated by discontinuing the medications and warming the patient using a warmed helium-oxygen mixture.

14 Claims, 6 Drawing Sheets

U.S. PATENT DOCUMENTS

| | | | |
|---|---|---|---|
| 6,303,156 B1 | 10/2001 | Ferrigno | 424/673 |
| 6,536,429 B1 | 3/2003 | Pavlov et al. | 128/203.26 |
| 6,547,811 B1 | 4/2003 | Becker et al. | 607/105 |
| 6,694,977 B1 * | 2/2004 | Federowicz et al. | 128/204.18 |
| 2002/0023640 A1 * | 2/2002 | Nightengale | 128/200.24 |
| 2002/0153010 A1 * | 10/2002 | Rozenberg et al. | 128/203.12 |
| 2003/0194378 A1 * | 10/2003 | Rogueda | 424/45 |
| 2004/0118407 A1 * | 6/2004 | Kandler | 128/207.14 |
| 2004/0149284 A1 * | 8/2004 | Smith et al. | 128/203.16 |

FOREIGN PATENT DOCUMENTS

| | | |
|---|---|---|
| WO | WO 99/66938 | 12/1999 |
| WO | WO 00/18459 | 4/2000 |

OTHER PUBLICATIONS

Sadowski, B. and M. Konarzewski, "Analgesia in Selectively Bred Mice Exposed to Cold in Helium/ Oxygen Atmosphere" Physiology & Behavior, vol. 66, No. 1, pp. 145-151 (1999).

Schmid-Elsaesser, Robert. et al. "Combination Drug Therapy and Mild Hypothermia, A Promising Treatment Strategy for Reversible, Focal Cerebral Ischemia." STROKE, vol. 30, No. 9, pp. 1891-1899, (1999).

"Composition of Air" http://mistupid.com/chemistry/aircomp.htp. (1991).

"Ice Slurry Heart Treatment gets $4 Million Dollar Boost," http://www.anl.gov/OPA/news02/news020913.htm.

"What is Liquid Ventilation.," http://www.med.umich.edu/liquid/whatislv.html.

*Therapeutic Hypothermia After Cardiac Arrest*, "ILCOR Advisory Statement," Nolan et al., 2003, pp. 118-121.

*Chill Therapy is Endorsed for Some Heart Attacks, New York Times*, nytimes.com. McNeil Jr., Donald G., Jul. 8, 2003, pp. 1-3.

Hozer, "Mild Therapeutic Hypothermia to Improve the Neurologic Outcome After Cardiac Arrest," N Engl J Med, vol. 346, No. 8, Feb. 21, 2002, pp. 549-556.

Bernard et al., "Treatment of Comatose Survivors of Out-Of-Hospital Cardiac Arrest with Induced Hypothermia," N Engl J Med, vol. 346, No. 8, Feb. 21, 2002, pp. 557-563.

Safar, et al., "Therapeutic Hypothermia After Cardica Arrest," N Engl J Med, vol. 346, No. 8, Feb. 21, 2002, pp. 612-613.

Ragaller, et al., "Perfluorocarbon aided gas exchange," Proceedings of the $1^{st}$ Postgraduate Course on Mechanical Ventilation, Department of Anaesthesiology and Intensive Care Medicine, University Hopsital Carl Gustav Carus, Technical University of Dresden, Germany.

Beran, et al., "An Improved Method for Inducing Hypothermia and Rewarming," Aviation Space and Environmental Medicine, Aug., 1979, vol. 50, No. 8, pp. 844-846-.

Beran, et al., "Hypothermia and rewarming induced by surface and He-$O_2$ inhalate temperature control," Journal of Applied Physiology, Aug. 1976, vol. 39, No. 2, pp. 337-340.

Musacchia, et al., "Helium-Cold Induced Hypothermia in the White Rat," Proceedings of the Society for Experimental Biology and Medicine, vol. 142, No. 3, Mar. 1973, pp. 734-739.

\* cited by examiner

INDUCING HYPOTHERMIA AND REWARMING USING A HELIUM-OXYGEN MIXTURE

RELATED APPLICATIONS

The present application claims priority to U.S. Provisional Patent Application Ser. No. 60/336,668, titled A NOVEL METHOD TO INDUCE AND MAINTAIN HYPOTHERMIA, filed Dec. 4, 2001; U.S. Provisional Patent Application Ser. No. 60/377,335, titled A NOVEL METHOD TO INDUCE HYPOTHERMIA AND REWARMING, filed Apr. 30,2002; and U.S. Provisional Patent Application Ser. No. 60/405,137, titled INDUCING HYPOTHERMIA AND REWARMING USING A HELIUM-OXYGEN MIXTURE, filed Aug. 22, 2002, all herein incorporated by reference in their entireties.

FIELD OF THE INVENTION

The present invention relates generally to medical devices and methods. More specifically, the present invention includes methods and devices for cooling and/or heating a human being body by providing cold and warm gases for respiration. The present invention includes methods and devices for rapidly and intentionally inducing hypothermia in a human being, from ambulance through operating room, for purposes including decreasing tissue oxygen consumption in order to increase the likelihood of survival and decrease cell damage following ischemic events, including heart attack or stroke.

BACKGROUND OF THE INVENTION

Deliberate lowering of the body temperature, or "induced hypothermia", as a therapeutic modality was first described by Talbot in 1941. (Talbot J H: The Physiologic and Therapeutic Effects of Hypothermia. N Engl J Med 224:281, 1941). The National Academy of Sciences published the investigational report on the physiological effects of hypothermia in 1955. (Dripps, R D, Ed: The Physiology of Induced Hypothermia. Washington, D.C., National Academy of Science Publication 451, 1956). These studies established that when cooled, the body's metabolism decreases at about 8% per degree Celsius and drops to one-half the normal at 28° C. Such a reduction in metabolism renders metabolically active organs such as the brain and heart less susceptible to periods of ischemia and hypoxia. As a result of this protective effect, hypothermia is used in heart surgery, brain surgery, spine surgery, aortic surgery, organ transplantation surgery, prevention of cerebral palsy, and treatment of strokes and heart attacks. Despite the expanding role of hypothermia in clinical settings, the methods to induce and maintain hypothermia remain primitive, cumbersome, unpredictable and dangerous.

Cooling the external surface of the body in order to cool the core of the body has been practiced for several centuries. Placing the body in a cold environment, rubbing alcohol on the skin, and placing cold sponges over various parts of the body are still practiced to lower the body temperature. These methods may work to lower fever, but they are unreliable and inefficient to induce hypothermia in a normothermic body. In the 1950's, patients were immersed in iced water to cool and warm water to warm. This involved wheeling full length tubs into the operating room next to the operating table and lowering the patient into the tub, still attached to all the monitoring wires, intravenous lines, arterial lines and breathing tubes. (Churchill-Davidson H C, McMillan I K R, Melrose D C, et al.: Hypothermia: Experimental Study of Surface Cooling. Lancet 2:1011, 1953). This method was dangerous to the patient because of the potential to disconnect intravenous lines, arterial lines, and breathing tubes, aspiration of water, and short-circuiting of monitoring wires. This cooling was cumbersome, erratic and unpredictable. Once the patient was taken out of the cooling tub and placed on the operating table, there was no way to maintain hypothermia because the body reflexively begins to rewarm. The surgeons had to operate quickly or risk damage to heart, brain, and other vital organs.

The limitations of cooling tubs gave rise to cooling blankets. In this method the patient is covered with a blanket that is cooled by circulation of cooled water or other fluid. Cooling of the body occurs slowly and erratically by this method. Ice bags are often placed in the armpits and groin to hasten the cooling process. Access to the patient is difficult with the cooling blanket in place. If the patient needs nursing care, surgical or other procedures to be performed, then the cooling blanket must be removed, resulting in reflex rewarming of the body. In addition to the problems noted in cooling tubs, excessive application of cooling blankets to lower the body temperature to the desired degree could result in frostbite and poor circulation to the limbs.

Extracorporeal cooling involves draining blood out of the body, cooling it to the desired temperature, and pumping it back into the body. Currently, the most effective means of extracorporeal cooling is through cardiopulmonary bypass. In this procedure, the venous blood is taken out of the body, cooled, oxygenated and pumped back into the patient's arterial system. The most common form of extracorporeal circulation used in cardiac and brain surgery involves draining venous blood from the vena cavae and pumping cooled, oxygenated blood into the ascending aorta. If oxygenation is not required and only mild to moderate hypothermia is desired, venous blood may be drained from a peripheral vein, cooled and returned to a peripheral artery.

Cardiopulmonary bypass is a complex procedure involving major thoracic surgery and cannot be maintained for more than a few hours. Some of the potential complications of cardiopulmonary bypass includes pain, surgery, infection, excessive bleeding, aortic dissection, cardiac distension, pericardial tamponade, venous obstruction, brain swelling, brain damage from ischemia and inadequate perfusion, air and clot embolism to brain and other organs, poor oxygenation, retention of carbon dioxide, excessive cooling, depletion of clotting factors and platelets, renal failure, abdominal hemorrhage, ascites, abdominal distension, hypertension, hypotension, and anaphylactoid reaction. In addition, the complex system of tubing, filters, oxygenator, heat exchanger, bubble catcher and the pump are prone to malfunction and breakdown. These limitations make it impossible to maintain cardiopulmonary bypass for more than a few hours, often the duration of a heart or brain operation.

Various forms of cooling devices can be placed inside a vein or an artery to cool the blood as it passes around such device. Cooling of the body with such devices is slow and unpredictable. Surgery is required to place these devices inside a major blood vessel and risk damage to the vessel, bleeding, thrombosis, infection, mechanical obstruction to blood flow, edema, disseminated intravascular coagulation (DIC) and ischemia to distal organs.

In an ischemic event, the blockage results in the death of cells immediately downstream of the blockage within minutes, in a primary cell death area. The dead cells release chemicals that induce collateral blood supplies to be opened in the direction of the primary cell death in an attempt to supply the oxygen-deprived area. The collateral blood openings require time to be formed, too long a time to save the cells in the secondary area using current treatments. Cells in the secondary cell area near the primary area then die in a cascade of cell death. Primary cell death in the brain causes cell expansion within the closed space of the skull, causing a cascade of cell death into secondary areas. The secondary cell death creates more expanding cells and increased pressure within the skull. The increased pressure within the skull reduces blood supply by constricting blood vessels at the very time that increased blood supply is most needed.

The cascade of cell death can greatly increase the size of the infarct region. In cardiac ischemic events, the increased infarct region size can mean an increased area that can later cause arrhythmias, and can lead to heart failure. In brain ischemic events, the increased number of dead cells can mean the difference between a small stroke, and not talking or walking again. What would highly desirable are methods for reducing the cascade of cell death, limiting the damage of heart coronary artery blockages, and limiting the damage caused by strokes. For the reasons earlier described, improved methods and devices for heating and cooling patients would be most advantageous.

SUMMARY OF THE INVENTION

The present invention includes methods of cooling and warming the human being body. Using the described method, the body may be cooled from normal physiological temperature (37° C.) to lower temperatures, or from an elevated body temperature to a normal physiological temperature. The method may also be used to warm a cold body back to normal physiological temperature.

The invention includes methods to cool and rewarm the human body. The lungs are used as a heat exchange source for cooling and heating the body. Helium, mixed with air or oxygen in varying concentration, can be used as the heat transfer medium. Cooling devices and heating elements connected to the breathing circuit heat or cool the inspired gases as required. Atomized liquid may be added to the gas stream to use evaporative heat loss from the liquid, for example, perfluorocarbons, administered into the lungs. When cooling the body, medications can be administered to suppress reflex heat production. Hypothermia may be terminated and the body rewarmed in some methods by raising the temperature of the helium-oxygen mixture, for example, up to 55° C. During rewarming, the inspired gases may be humidified to minimize evaporative heat loss from the lungs. Pharmacological agents that depress heat production may be discontinued, if clinical situations permit, to allow the body to regenerate heat.

The present invention describes a novel methodology to induce and maintain hypothermia in humans and other human beings. The method includes: (1) use of lungs for heat exchange; (2) use of cooled gases for ventilation; (3) use of helium in the ventilation gas mixture; (4) use of liquid atomized perfluorocarbons to achieve evaporative cooling from the lungs; and (5) use of medications to control reflex heat production. Hypothermia is achieved through loss of heat from the lungs. The large surface area of the pulmonary alveolus is utilized to exchange heat from the body to inspired gases. In the lungs, blood comes in close proximity to the inspired gases, being separated by the alveolar membrane only a few microns in thickness. The gossamer thinness and the large surface area of the lungs are ideally suited for heat exchange. The patient may be allowed to breathe spontaneously or be mechanically ventilated; transferring heat to the inspired gases; and the heat is carried away with the expired gases.

This heat loss is further enhanced by lowering the temperature of the inspired gases. As per the laws of thermodynamics, the heat exchange between the blood in the lung alveoli and the inspired gases is directly proportional to the temperature difference between them. However, in the present invention, the inspired gases are preferably not cooled below 0° C. to prevent crystallization of water in the cells of the respiratory tract. To the inspired gas mixture, helium is added to improve the rate of heat transfer. The thermal conductivity and thermal diffusivity of helium is much greater than other biologically compatible gases such as oxygen, nitrogen, or carbon dioxide. As a result, more of the inspired gases equalize with the body temperature within the duration of each breath. This results in greater heat loss from the body than otherwise possible with air or other gas mixtures. In order to avoid hypoxemia, the concentration of oxygen in the inspired gas mixture is preferably kept to at least 20%, with the remainder of the gas mixture preferably being helium. The heat loss from the lungs is intensified by addition of perfluorocarbon mist or liquid to the inspired gases. The phase change of the perfluorocarbon from liquid from gas extracts a significant amount of heat from the lungs due to the latent heat of vaporization. Since the heat transfer rate between the walls of the tracheobronchial tree and the droplets of perfluorocarbon is increased by helium, the mixture of heliox and perfluorocarbon works synergistically to amplify heat loss from the lungs. Other vapors and gases may be added to the helium-oxygen mixture, if clinical circumstances warrant.

Medications may be administered to prevent the body's reflex heat production mechanisms that are activated when the body is cooled. This includes medications to suppress the thermoregulation center located in the brain and to suppress peripheral heat production in the skeletal muscles, liver, kidney, adipose tissue and other cellular structures. General anesthetics, narcotics, and anti-serotonin agents may be administered to suppress the central heat regulation center; while muscle relaxants, antithyroid agents and sympatholytic agents may be used to decrease peripheral heat production.

One exemplary method includes administering morphine and propranolol to a patient, inserting an insulated endotracheal tube and instituting mechanical ventilation of the lungs to provide one and a half to twice the minute ventilation, using an inspired gas mixture, of 21% oxygen and 79% helium, which has been cooled to 4° C. Applicants' animal studies show that cooling of the body's core temperature occurs at a rate of 0.15–0.3° C. per minute. This rate can be nearly doubled to 0.5 degrees C per minute when a 1% mist of perfluorocarbon is added to the cooled helium-oxygen mixture. The desired level of hypothermia can be maintained by tapering the concentration of perfluorocarbon mist, and altering the minute ventilation and temperature of the helium-oxygen mixture. Hypothermia may be terminated by discontinuing the medications and warming the helium-oxygen mixture.

In one method according the present invention, body temperature in a human being is lowered, wherein the method comprises cooling inspired gases to a temperature below body temperature, and providing the cooled gases to a patient, thereby using the lungs for heat exchange, and lowering the patient's body temperature. The method preferably includes helium in the gases in order to increase the heat transfer rate. The cooled gases are preferably cooled to a temperature greater then about 1 degree Centigrade, most preferably about 4 degrees Centigrade or above. The cooled gases are preferably provided through a face mask or endotracheal tube, most preferably through an insulated tube coupled to the face mask or endotracheal tube. Methods preferably include administering drugs that suppress reflex heat production by the human being body when cooling occurs.

In another method according the present invention, body temperature in a human being is increased, wherein the method comprises warming inspired gases to a temperature above body temperature, and providing the warm gases to a patient, thereby using the lungs for heat exchange, and raising the patient's body temperature. The method preferably includes helium in the gases in order to increase the heat transfer rate. The warm gases are preferably warmed to a temperature not greater than about 55 degrees Centigrade. The warm gases are preferably provided through a face mask or endotracheal tube, most preferably through an insulated tube coupled to the face mask or endotracheal tube. Intensification of heating the blood flowing through the lungs can be achieved by addition of perfluorocarbon mist to the inspired warm helium-oxygen mixture. As significant amount of heat can be released into the lungs, if the perfluorocarbon vapor condenses from gas to liquid. This process can take advantage of the latent heat of condensation of the perfluorocarbon vapor. Methods preferably include administering drugs that promote heat production, and/or counter the effects of drugs that suppress reflex heat production.

The heating and cooling methods can include heating and cooling using insulated breathing circuits and insulated endotracheal tubes. The insulation can vary between about 2 mm and about 2 cm in some embodiments. Some devices have at least 2 mm of insultation and some less than about 4 cm of insulation. Some methods include use of a cooling device attached to the breathing circuit. The cooling device may be attached to the inspiratory and/or the expiratory limb of the breathing circuit. The present invention includes use of a device to bleed helium in varying amounts into the inspiratory limb of a breathing circuit, so as to alter the concentration of helium in the inspired gases. The present invention includes the use of medications to suppress reflex heat production. The present invention also includes warming a Heliox gas mixture to a temperature warmer than body temperature and providing the warm Heliox to patients to ventilate patients in order to treat COPD, emphysema, and bronchial asthma.

Body temperature can be further cooled by atomizing and injecting a fluid into the helium-oxygen gas mixture. The fluid is preferably a biocompatible liquid cooled to a temperature below body temperature, below 37° C., atomized, and injected into the helium and/or oxygen gas stream. This injection can be outside of the body, into the inspiratory limb of the breathing circuit. The cooled, atomized liquid can also be injected into the helium-oxygen gas stream well within the patient, for example, within the breathing tube. The liquid can also be atomized external to the body and injected within the lungs. A 1% by volume mist is used in some embodiments. The liquid selected preferably has a diffusivity and solubility of oxygen and carbon dioxide sufficiently large to sustain life when the fluid is injected in atomized form into the lungs. The diffusivity and solubility of oxygen and carbon dioxide are preferably sufficiently larger than water to allow needed exchange of oxygen and carbon dioxide across a boundary layer of the selected liquid in the aveoli. In a preferred embodiment, the liquid is a perfluorocarbon. The perfluorocarbon preferably has a boiling point of less than body temperature, less than 37° C. The perfluorocarbon more preferably has a boiling point of less than 34° C. One perfluorocarbon selected has a boiling point of about 30° C.

The atomized perfluorocarbon, for example, atomized by a nebulizer, ultra-sonic device, or jet injector, has preferably first been cooled to a cold temperature, for example, about 0° C. The cooled, atomized liquid, such as a perfluorocarbon, can then be injected into the helium-oxygen gas stream either inside or outside of the body. As the cooled, atomized, perfluorocarbon enters the lungs, the cold liquid can cool the aveoli due to the cold temperature of the liquid. The liquid can be atomized sufficiently small so as to enter smaller bronchioles, and even into aveoli. The mist preferably has an average diameter of less than about 10 microns, and more preferably has an average diameter of less than about 4 microns. One combination uses about 1 gram of perfluorocarbon per 100 cubic centimeters of helium-oxygen gas mixture. One perfluorocarbon used is FC-87, available from 3M Corporation.

Applicants believe that the atomized, cooled liquid may form a boundary layer within the bronchioles and aveoli, while allowing the diffusion of dissolved oxygen and carbon dioxide across the boundary layer. This increased diffusivity and solubility of oxygen and carbon dioxide relative to water is believed to be the reason why human beings will drown when the lungs are filled with water, but can breathe when the lungs are filled with oxygenated perfluorocarbons. While the preferred embodiment of the invention utilizes perfluorocarbons, the invention also includes other fluids that have sufficiently high oxygen and carbon dioxide solubility to sustain life during the procedure.

In some methods, applicants believe that the atomized, cooled, liquid mist within the lungs can form a boundary layer within the aveoli and smaller bronchioles, and then be vaporized into the vapor form. The mist can thus cool the, lungs through both the conduction of heat from the lungs to the cooler liquid, and through the latent heat of vaporization supplied by the lungs to the liquid. The now vaporized material can then be expelled from the lungs. The combined effect of having aveoli filled with helium-oxygen gas mixture that rapidly transfers heat, together with cold and vaporizable liquids such as perfluorocarbons, can act synergistically to rapidly cool the body.

The present invention includes a method to lower the body temperature in a human being, which method comprises the steps of: using the lungs for heat exchange; use of helium in the gas mixture of ventilation gases; cooling the inspired gases to varying degrees below body temperature; and, administration of drugs that suppress reflex heat production by the human being body when cooling occurs.

The present invention includes a method to raise the body temperature in a human being, which method comprises the steps of: using the lungs for heat exchange; use of helium in the gas mixture of ventilation gases; heating the inspired gases to varying degrees above body temperature; and administration of drugs that promote heat production, or counter the effects of drugs that suppress reflex heat production.

In some methods, the carbon dioxide is added to the gas mixture in an amount titrated by measured end tidal carbon dioxide levels and/or measured arterial blood gas. The carbon dioxide can be measured in the human being's blood, and carbon dioxide added to the gas mixture as a function of the measured amount of carbon dioxide in order to maintain normal levels of carbon dioxide. In some methods, carbon dioxide is measured in the human being's exhaled gases, and carbon dioxide is added to the gas mixture as a function of the measured amount of carbon dioxide in order to maintain normal levels of carbon dioxide. In some embodiments, the gas mixture comprises between about 3 to 5 volume percent carbon dioxide, 72 to 75 volume percent helium, and about 20 volume percent oxygen. Methods can further comprise disposing a cooling blanket over the human being and blowing cold air over the human being, the cold air having a temperature of less than room temperature.

The present invention also includes a method for raising the body temperature in a human being the method comprising: providing an oxygen containing gas mixture; heating the oxygen containing gas mixture to a temperature higher than body temperature; and respirating the human being using the heated gas mixture. The method can include the oxygen containing gas mixture including helium gas in the mixture. The gas mixture can include at least about 50 percent helium by volume. The gas mixture can include about 80 percent helium by volume. In some methods, the heating includes heating the gas mixture to a warm temperature selected from the group of temperature ranges consisting of: at least about 38 degree C., at least about 40 degrees C., at least about 42 degrees C., at least about 44 degrees C., between about 40 degree C. and about 44 degrees C., and between about 40 degree C. and about 55 degrees C. In some methods, the respirating step includes supplying the heated gas mixture through an endotracheal tube or face mask. The respirating step can includes supplying the heated gas mixture through an insulated tube to an endotracheal tube or face mask.

In some warming methods, the method further comprises administering drugs that promote heat production and/or counter the effects of drugs that suppress reflex heat production, and combinations thereof. Some methods use a device to bleed helium in varying amounts into the inspiratory limb of a breathing circuit, so as to alter the concentration of helium in the inspired gases. The methods can include providing a heating unit and coupling the heating unit to the inspiratory limb of a breathing circuit, such that the gas mixture passes through the heating unit and is warmed. The gas mixture can include between about 0.5 percent carbon dioxide and 5 percent carbon dioxide by volume.

In some warming methods, the carbon dioxide is added to the gas mixture in an amount titrated by measured end tidal carbon dioxide levels and/or measured arterial blood gas. The carbon dioxide can be measured in the human being's blood, and carbon dioxide is added to the gas mixture as a function of the measured amount of carbon dioxide in order to maintain normal levels of carbon dioxide. The carbon dioxide can be measured in the human being's exhaled gases, and carbon dioxide is added to the gas mixture as a function of the measured amount of carbon dioxide in order to maintain normal levels of carbon dioxide. In some warming methods, the gas mixture comprises between about 3 to 5 volume percent carbon dioxide, 72 to 75 volume percent helium, and about 20 volume percent oxygen.

The present invention includes a system for inducing hypothermia in humans and/or human beings, the system comprising: a first gas intake for coupling to a gaseous oxygen source; a second gas intake for coupling to a gaseous helium source; a mixing region coupled to the first and second gas intakes for combining the oxygen and helium to produce a gas mixture; a cooling region in fluid communication with the mixing region for cooling the oxygen and helium; and a gas outlet in fluid communication with the cooling region for operably coupling the cooled gas mixture to a breathing tube or endotracheal tube or face mask tube.

In some systems, the cooling region is disposed to cool the helium and oxygen before mixing. In other systems, the cooling region is disposed to cool the helium and oxygen after mixing. Systems can include a recirculation loop for receiving the exhaled gases from the patient, removing or scrubbing at some of the carbon dioxide from the exhaled gases, and adding the scrubbed exhaled gases to newly added oxygen and helium gases. Systems can include a pin index coupling for coupling specifically to helium and oxygen cylinders or sources. Systems can also include a device for injecting a perfluorocarbon into the gas mixture. Some systems include a controller for controlling the cooling region output temperature responsive to a temperature measured near the patient. Systems according to the present invention can further include a ventilator for providing a positive pressure gas mixture to the patient. A scavenging system coupled to receive gases exhaled from the patient is provided in some embodiments. Some systems include tubing for conveying the oxygen, helium, and gas mixture, wherein at least some of the tubing is insulated to substantially reduce warming of the gas mixture from the room temperature.

The present invention includes a system for warming humans, the system comprising: a first gas intake for coupling to a gaseous oxygen source; a second gas intake for coupling to a gaseous helium source; a mixing region coupled to the first and second gas intakes for combining the oxygen and helium to produce a gas mixture; a heating region for heating the oxygen and helium; and a gas outlet for operably coupling the heated gas mixture to a breathing tube or endotracheal tube or face mask tube. In some systems, the heating region is disposed to heat the helium and oxygen before mixing. In other systems, the heating region is disposed to heat the helium and oxygen after mixing. Some systems include a recirculation loop for receiving the exhaled gases from the patient, removing or scrubbing at some of the carbon dioxide from the exhaled gases, and adding the scrubbed exhaled gases to newly added oxygen and helium gases. Systems can also include a ventilator for providing a positive pressure gas mixture to the patient. A scavenging system coupled to receive gases exhaled from the patient can also be provided. Tubing for conveying the oxygen, helium, and gas mixture can include at least some of the tubing being insulated to substantially reduce cooling of the gas mixture from the room temperature.

Another aspect of the invention includes a composition of matter comprising: helium gas; oxygen gas; and a perfluorocarbon liquid having a boiling point of less than 37 degrees centigrade. The composition of matter can have the helium gas present in a concentration of at least 50 volume percent. Some composition have the oxygen gas is present in a concentration of at least 17 volume percent. In some compositions, the perfluorocarbon is biocompatible. The perfluorocarbon is present as droplets in the helium and oxygen gas in some embodiments. The droplets in some compositions can have an average droplet diameter of less than about 10 microns. In some compositions, at least some of the helium and oxygen gases are dissolved in a substantially continuous perfluorocarbon phase. In some compositions, at least some of the helium and oxygen gases are in entrained gas bubbles in a substantially continuous perfluorocarbon phase.

The present invention also includes a composition comprising a helium gas and oxygen gas mixture having a temperature of less than 10 degrees Centigrade, greater than 40 degrees Centigrade, or more than about 3 degrees Centigrade away from body temperature, for use in therapy. The composition can have a temperature of less than 5, 10, or 15 degrees Centigrade, depending on the embodiment. In some compositions of matter, the helium gas is present in a concentration of at least 50 volume percent and the oxygen gas is present in a concentration of at least 17 volume percent. The composition can further comprise a liquid having a boiling point of less than 37 degrees Centigrade. In some embodiments, the liquid is a fluorocarbon. The liquid can have an oxygen solubility at least twice that of water. In some compositions, the helium and oxygen gas mixture is a substantially continuous phase wherein the liquid comprises droplets disposed in the gas. The fluorocarbon droplets have an average droplet diameter of less than about 10 microns in some compositions. In other compositions, the liquid is a substantially continuous phase, wherein the gas is dissolved and/or entrained in the liquid. In other compositions, the liquid is a substantially continuous phase, wherein the gas comprises bubbles disposed in the liquid. The present invention includes a composition comprising helium gas and oxygen gas having a temperature of less than 10 degrees Centigrade for use in treating an ischemic event or ischemia.

The present application includes a method for inducing hypothermia a patient, the method comprising: introducing an amount of liquid perfluorocarbon cooled to a temperature of less than 10 degrees Centigrade into the patient's lungs, wherein the amount is at least about half the end tidal volume of the patient's lungs; and ventilating the patient's lungs with a gas mixture comprising helium and oxygen having a temperature of less than 10 degrees Centigrade. In some compositions, the liquid has a boiling point of less than 37 degrees Centigrade. In some embodiment compositions, the liquid temperature is less than 5 degrees Centigrade. The liquid temperature is between 0 and 4 degrees Centigrade in some compositions. The gas temperature is less than 5, 10, or 15 degrees Centigrade in various embodiments, and between 0 and 4 degrees Centigrade in other embodiments.

The present invention includes methods for inducing hypothermia in a human patient, the method comprising performing partial liquid ventilation on the patent using a liquid perfluorocarbon having a temperature less than 5, 10, or 15 degrees Centigrade and a gas comprising helium and oxygen and having a temperature of less than 5, 10, or 15 degrees Centigrade, depending on the embodiment.

The present invention includes a method for inducing hypothermia in a human patient, the method comprising performing partial liquid ventilation (PLV) on the patent using a liquid having a temperature less than 10 degrees Centigrade and a gas comprising helium and oxygen and having a temperature of less than 10 degrees Centigrade, wherein the liquid has an oxygen solubility and carbon dioxide solubility sufficient to sustain the patient's life during the PLV procedure.

The present invention further includes an adopter for use with an endotracheal tube, the adopter comprising: a tubular elbow including a tube wall, a first tubular region for coupling to a gas source coupled to a bend, the bend being coupled to a second tubular region for coupling to an endotracheal tube proximal portion, wherein the second region has a second region inside diameter; and a port formed into the tube wall having a port inside diameter, wherein the port inside diameter is at least one-third the second region inside diameter. On one adopter, the port is disposed within a nipple extending outward from the tube wall. In one embodiment, the adopter second tubular region has a central axis and the port has a central axis that is substantially aligned with the second region central axis. In some such adopters, the port is coaxially aligned with the central region. In other adopters, the port is disposed within a tube extending outward from the tube wall and inward from the tube wall into the adopter interior. An adopter can further comprise an atomizer extending from the second region so as to be disposed within the endotracheal tube, wherein the atomizer is in fluid communication with port.

DETAILED DESCRIPTION OF THE PREFERRED EMBODIMENTS

Figure 1:
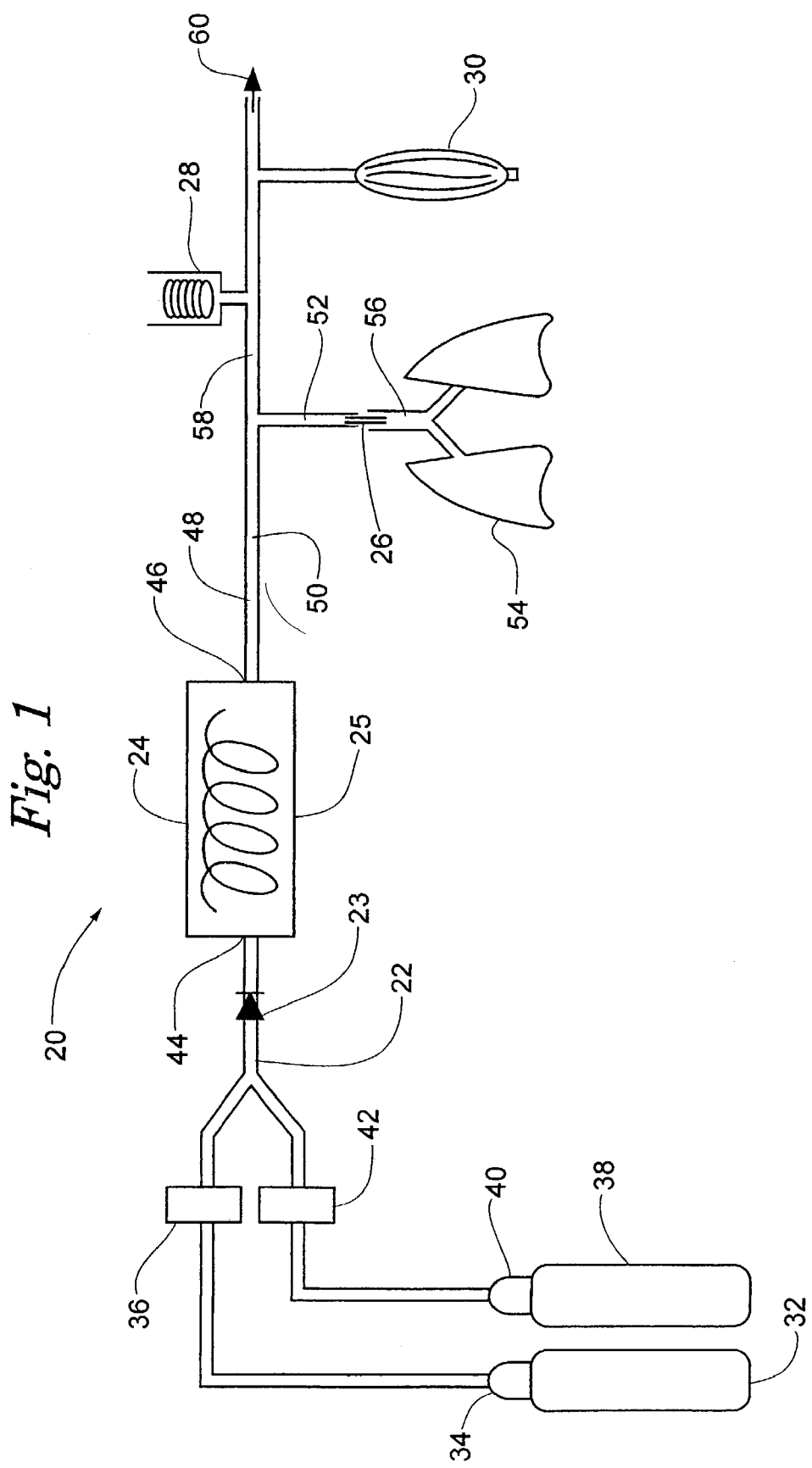
FIG. 1 is a schematic representation of a cooling/warming system having helium and oxygen coupled to a cooler/heater providing cooled/warmed gases to a ventilation system coupled to a patient's lungs.

The following detailed description should be read with reference to the drawings, in which like elements in different drawings are numbered identically. The drawings, which are not necessarily to scale, depict selected embodiments and are not intended to limit the scope of the invention. Several forms of invention have been shown and described, and other forms will now be apparent to those skilled in art. It will be understood that embodiments shown in drawings and described above are merely for illustrative purposes, and are not intended to limit scope of the invention as defined in the claims that follow.

The present invention includes methods for inducing and maintaining hypothermia in human beings. Other, modified methods, permit rewarming of cooled human beings. One method includes-five steps or stages to achieve reduction in body temperature: (1) use of the lungs as the means of heat exchange; (2) use of varying concentrations of helium in the inspired gases to facilitate rapid and effective heat exchange between the inspired gases and the blood in the lungs; (3) cooling the inspired gases to extract heat from the blood in the lungs, and warming the inspired gases to rewarm the blood flowing through the lungs; (4) use of perfluorocarbon mist or vapor to exploit the latent heat of vaporization for cooling and latent heat of condensation for warming, respectively; and (5) use of medications to suppress or blunt the body's inherent attempts to rewarm itself when cooled.

While the devices, methods, and systems of the present invention are preferably used on human patients, the present invention may be used on other mammals.

Use of the Lungs for Heat Exchange

Heat loss from the lungs occurs by conduction, convection and evaporation of water from the lungs. The anatomical structure and the physiological functioning of the lungs render them to be excellent heat transfer organs. The lungs are made up of approximately 500 million alveoli that span a surface area of nearly 100 square meters. These alveoli are richly supplied with blood capillaries whose surface area is approximately 70 square meters. The alveolar membrane which separates the air in the alveolus from blood in the capillaries is extremely thin and composed of an alveolar epithelium, a fused epithelial and endothelial basement membrane, and a capillary endothelium. This highly attenuated alveolar membrane may range in thickness from 0.5–10 µm. (Robert R. Mercer, James D. Crapo: Normal Anatomy and Defense Mechanisms of the Lung. Page 33, in Textbook of Pulmonary Diseases. Vol 1., 6th Edition. Edited by: Gerald L. Baum, James D. Crapo, Bartolome R. Celli, Joel B. Karlinsky, Publishers: Lippincott-Raven, Philadelphia-New York, 1998.) According to Fourier's Law of Heat Transfer, heat flux "q" is greatly accentuated by the thinness of the alveolar membrane.

$$q = k \frac{\Delta T}{L}$$

Where "k" is the thermal conductivity, $\Delta T$ is the temperature gradient, and "L" the thickness of the conducting medium. (John H. Lienhard: A Heat Transfer Textbook, 1981 by Prentice Hall, Inc., Engelwood Cliffs, N.J. 07632). The total amount of heat transferred, "Q" is directly proportional to the surface area "A".

Q=qA

In contrast to the lungs, surface area of the skin is only 1.7 to 1.9 square meters in an adult and the thickness varies from a few millimeters (2–3 mm) to few centimeters, if one includes the insulating layer of subcutaneous fat. Therefore, the inventors surmised that because of the large surface area and thinness of the alveolar membrane, the lungs are an excellent medium for conductive heat transfer from the blood in the capillaries to the inspired gases in the alveoli and vice versa.

Use of Varying Concentrations of Helium in the Inspired Gases

Heat conduction in the lungs is rarely at a steady state. With each breath, the temperature of the inspired air partially equilibrates with the body temperature. In order to achieve maximum heat transfer from the blood to the inspired air, the alveolar gas must not only conduct heat rapidly, but the alveolar gas should also warm toward body temperature before the expiration. This form of transient heat conduction, as opposed to steady state conduction, is called Thermal Diffusivity ($\alpha$). Diffusivity depends on thermal capacity of the medium and its thermal conductivity.

$$\alpha = \frac{k}{\rho c}$$

Where "$\rho$" is the density, "c" is the specific heat, and "$\rho c$" is the volumetric thermal capacity of the medium. Among the biologically compatible gases, helium appears to be best suited for rapid warming. As compared to nitrogen and oxygen, helium is nearly 8 times more efficient in diffusing heat. Hence, with each breath a mixture of helium would equilibrate with body temperature faster than air or pure oxygen. Heat loss would be greater with faster respiratory rate in a helium mixture, since warming of the inspired air would not be the rate-limiting step in heat loss from the lung.

Oxygen is vitally necessary for cellular metabolism. Inadequate oxygen in the inspired gas mixture would lead to fatal hypoxemia. Applicants recommend using a mixture of helium and oxygen, wherein the oxygen concentration is not less than 20% of the final mixture. If other agents, such as carbon dioxide, nitrogen, nitric oxide, and volatile anesthetic agents-are added to the mixture, care is preferably taken to ensure that oxygen levels do not drop below 20% in the final mixture. It is recommended that oxygen sensors be used to measure inspired concentration in each breath, irrespective of the mode of ventilation.

Hyperventilation using heliox (helium and oxygen mixture) may lead to lowering of the blood carbon dioxide levels. Undue lowering of carbon dioxide levels in blood may lead to diminished blood supply to the brain and alter the acid-base balance in the body. Small amounts of carbon dioxide may be added to the inspired gas mixture in order to maintain normal levels of blood carbon dioxide. Applicants recommend and prefer that no more than about 5% of the inspired gas mixture be carbon dioxide. End tidal carbon dioxide levels and arterial blood gases measurements may be utilized to titrate the amount of carbon dioxide added to the inspired gas mixture. One inspired gas mixture comprises 3–5% carbon dioxide, 72–75% helium and 20% oxygen. Oxygen levels must be increased if there is a threat of hypoxemia. Minute ventilation may be maintained at 1.5 to 3 times the normal rate.

Cooling the Inspired Gases

As stated by Fourier's Law, the heat flux resulting from thermal conduction is proportional to the magnitude of the temperature gradient. Hence, the heat loss from the body can be increased by lowering the temperature of the inspired gas so as to increase the temperature gradient. However, since water turns to ice at 0° C., cooling below this temperature may result in formation of ice crystals within the cells of the respiratory system. Ice crystals may disrupt cellular function and lead to organ failure and death. Applicants prefer and recommend maintaining the temperature of the inspired gas at no less than 1–4° C. The temperature is preferably monitored at the point of entrance into the respiratory system. In some embodiments, the temperature is monitored near the distal region of an endotracheal tube, so that the gas temperature is measured after the heating effects of the trachea are accounted for. The inspiratory gas may be cooled by any means known to one skilled in the art of refrigeration. For example, a small refrigeration unit may be added to the inspiratory limb of a ventilator to cool the inspired gas mixture to the desired temperature. Another option would be to cool the gases at their source, before they are piped into the circuit of the ventilator. Portable units may be attached to a ventilating bag. The temperature of the inspired gas may be maintained automatically by a feed back loop connected to a thermostat or manually controlled to maintain the desired temperature. The temperature may-be altered by changing the settings on the cooling unit or adding varying amount of warm gas to the inspired mixture. The patient's core body temperature can be monitored and used to control the degree of cooling. Target core body temperatures of between 28 and 32 degrees Centigrade are used in some methods, with target temperatures of less than 32, less than 30, or about 30 degrees Centigrade also being within the scope of the invention.

The body may be quickly rewarmed by heating the inspired gas mixture. As stated by Fourier's Law, the heat flux is proportional to the magnitude of the temperature gradient and opposite in direction of flow. Hence, if the inspired gas mixture is warmer than the body, heat will flow from the inspired gas to the blood in the lungs. Warmed circulating blood will gradually warm the rest of the body. Applicants do not recommend warming the helium-oxygen mixture beyond a temperature of 55° C. Higher temperatures may cause burn injury to the delicate cells of the respiratory system.

The inspired gas mixture may be warmed to the desired temperature by any means known to persons conversant in the art of designing heaters and humidifiers. For example, the heater may be added to the inspiratory limb of a breathing circuit or the gases may be heated at their source. A heated mixture of helium and oxygen may be particularly useful in rewarming after general anesthesia, induced hypothermia, and accidental hypothermia.

Perfluorocarbon (PFC) Injection

Perfluorocarbons (PFCs) may be atomized by any means known in the art. This could be gas driven, jet, high pressure, compressed gas, or ultrasonic nebulizer. The end result is the creation of mist composed of fine particles or droplets of PFC. The PFC mist is introduced into the heliox, either inside the lungs or outside the lungs. The heliox acts as the suspension medium for the PFC droplets. The heliox carries the PFC mist through the tracheobronchial tree into the terminal bronchioles and the alveoli.

The PFC may be injected into the tracheobronchial tree. Under pressure or along with a carrier gas, the PFC may be injected so as to achieve an atomized spray, directly within the tracheobronchial tree. For example, in one embodiment of the invention, a set amount of PFC is injected through a narrow tube with an atomizer tip that is located wholly within the inside of an endotracheal tube. This results in atomized PFC sprayed within the endotracheal tube. The injection and atomization may be timed to synchronize with the inspiratory phase of the ventilator.

The PFC mist may be added to the expiratory limb of a breathing circuit. In complex arrangements of the breathing circuits, such as the Maplesons Systems A-E, where there is variable amount of mixing of the inspired and expired gases, the PFC mist may be added to the expiratory limb of the breathing circuit. The mixed inspiratory-expiratory gases/heliox containing the PFC mist may be administered to patient through face mask, endotracheal tube or any other upper airway device used to deliver gases into the lungs.

FC87

The inventors investigated several perfluorocarbon chemicals to find suitable compounds that achieve an objective of safe use in the lungs to induce hypothermia. The authors found the FC 87 compound to be uniquely suited to induce hypothermia by inhalation through the lungs. FC87, according to the manufacturer, has the formula C5F12. (1) The FC 87 is bio-compatible. The investigators found no adverse histopathological changes in the vital organs of mice drowned in the chemical for several hours. (2) The FC 87 is a breathable liquid. Due to the enhanced solubility of respiratory gases in FC 87, mammals can breath the liquid into their lungs and maintain respiratory functions for a prolonged periods of time. The investigators found mice in bubble oxygenated FC 87 to survive submerged in the liquid for 9–15 minutes. In contrast mice died in bubble oxygenated water with in 1–2 minutes. (3) The physical properties of FC 87 are ideally suited for evaporative cooling from the lungs. FC 87 boils at 30° C. The chemical introduced into the lungs evaporates extracting heat from the lungs.

Example of Heat Carrying Capacity Calculations Using FC87

Addition of small amounts of phase-change material (FC87) can dramatically increase the heat carrying capacity of a gas stream. Here we compare the heat carrying capacity per unit volume of five different fluid systems. It is assumed that the fluids enter the lungs at 4° C. and heated to a specified temperature $T_{out}$. The relevant thermophysical properties are shown in Table 1.

TABLE 1

Thermophysical properties.

| Fluid | Density(kg/m$^3$) (kg/m$^3$) | Specific Heat (kJ/kgK) | Heat of Vap (kJ/kg) |
|---|---|---|---|
| Oxygen (300K) | 1 3007 | 0 92 | |
| Helium | 0.1906 | 5 2 | x |
| Nitrogen | 1 1421 | 1.0408 | x |
| FC87(vapor) | 12 26 | 1 0408 | x |
| FC87(liquid) | 1630 | 1.05 | 88 |

FC 87 is Manufactured by 3M Corporation, Minneapolis, Minn., USA. Properties of FC87 are obtained form 3M product literature.

The heat carrying capacity is calculated as follows:

For pure gases with no phase change:

$$Q=\rho_g c_{pg}(T_{out}-T_{in}). \quad (1)$$

For mist flows with a carrier gas and a phase-change fluid (FC87):

$$Q=(v_f\rho_{fc}c_{pfc}+(1-v_f)\rho_g c_{pg})(T_{out}-T_{in}) \text{ when } T_{out}<T_{bp} \quad (2a)$$

and $$Q=(v_f\rho_{fc}c_{pfc}+(1-v_f)\rho_g c_{pg})(T_{out}-T_{in})+\Delta H v_f\rho_{fc} \text{ when } T_{out}>T_{bp} \quad (2b)$$

where $v_f$—volume fraction of FC87
$\rho_{fc}$—density of FC87
$c_{pfc}$—specific heat of FC87
$\Delta H$—heat of vaporization of FC87

$\rho_g$—density of gas
$c_{pg}$—specific heat of gas
$T_{in}$—initial temperature
$T_{out}$—final temperature
$T_{bp}$—boiling point of FC87

We consider the following five cases for comparison:
Case#1: Pure oxygen
Case#2: Pure nitrogen
Case#3: Pure helium
Case#4: Helium with 1% FC87 mist
Case#5: Helium with 0.2% FC87 mist.

Figure 6:
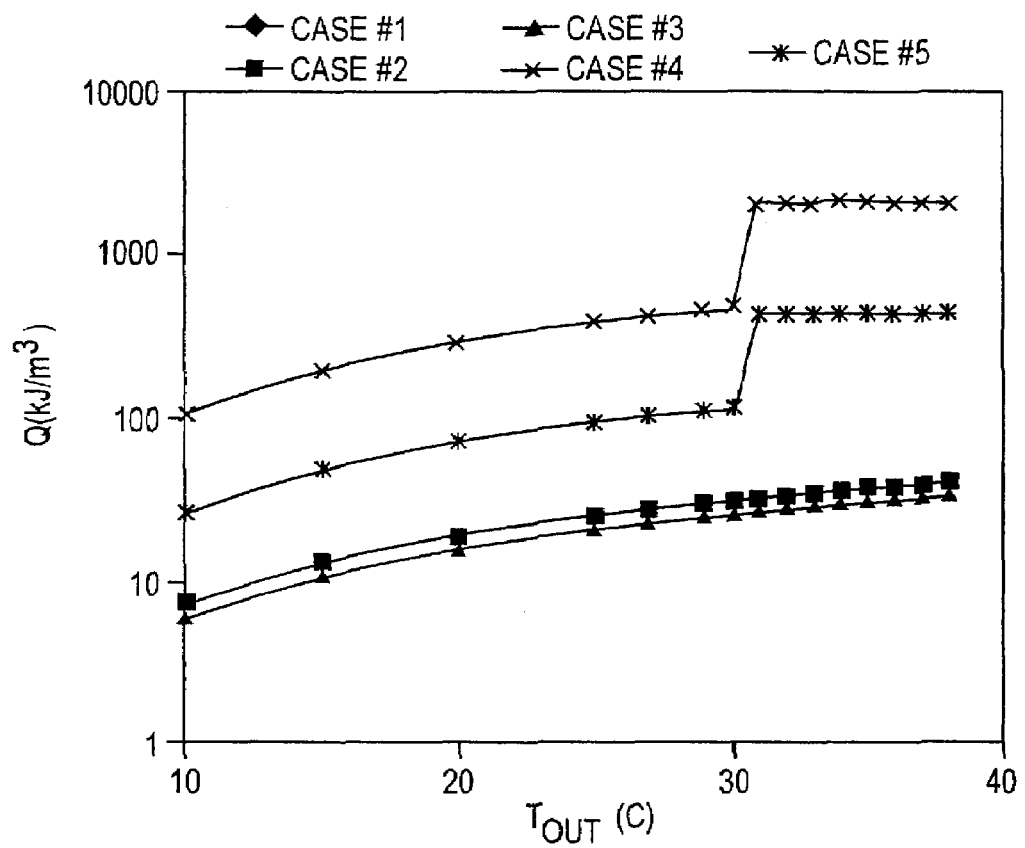
FIG. 6 is a graph showing the increase in heat carrying capacity with addition of 1% and 5% perfluorocarbon mist to respiratory gases.
Figure 7:
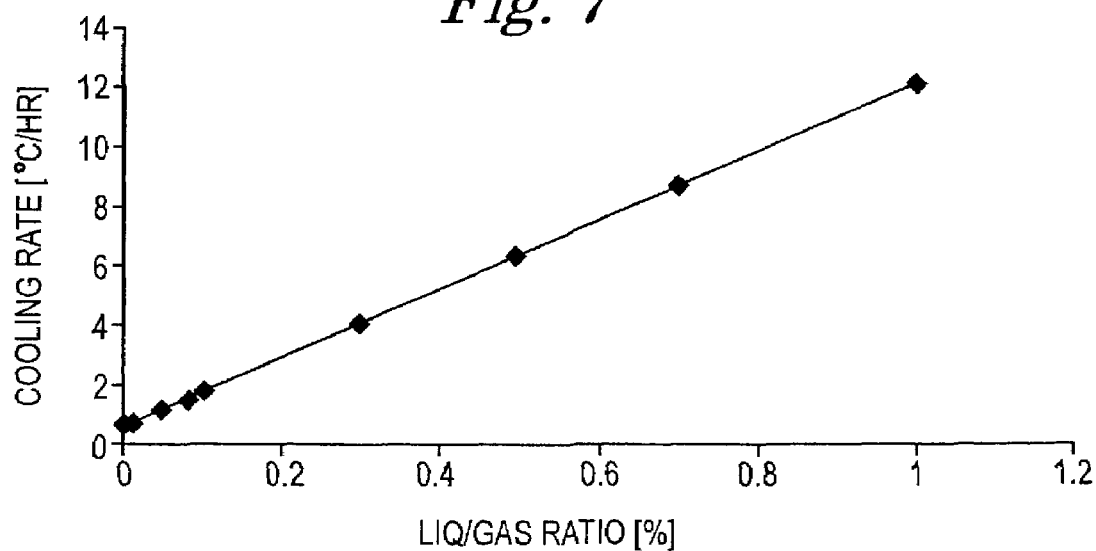
FIG. 7 is a graph showing the increase in theoretical cooling rate with increased perfluorocarbon concentration in heliox.

FIG. 6 shows the heat carrying capacity (kJ/m3) of the five different cases as function of outlet temperature $T_{out}$. Tin is taken to be 4° C. for the calculations shown in FIG. 6. Note that even a small amount (0.2% by volume) of FC87 addition to the inspired gases can dramatically increase their heat carrying capacity.

The perfluorocarbons may be atomized into fine droplets of varying diameters from fraction of a micron to several microns. The process may be achieved by any means known in the art. For example, perfluorocarbons may be nebulized using ultra sound, or high pressure injection through a fine nozzle. The atomization may involve only the perfluorocarbon being injected through a fine nozzle (single fluid atomization); or mixed with carrier gas prior to being injected through a fine nozzle (twin fluid atomization). The carrier gas may be room air, nitrogen, oxygen, helium, carbon-dioxide, or any other suitable vapor or gas or mixture.

The perfluorocarbon mist could be cooled by any means known in the art of refrigeration. The maximum heat extraction was noted when the temperature of the perfluorocarbon mist at the point of entry into the lungs was between −10° C. and 4° C. The perfluorocarbon could be cooled prior to atomization or after atomization. The mist could also be allowed to cool by the carrier mixture of cooled helium and oxygen.

Varying concentrations of perfluorocarbon mist could be added to the inspiratory gas flow of a respiratory circuit. The authors find substantial heat transfer intensification even at 0.002% to 5% volume concentration of liquid perfluorocarbons in the inspiratory gases. The perfluorocarbon mist could be delivered to the lungs through an endotracheal tube or suitable airway mask. The atomization may occur inside the trachea or outside. Nebulized perfluorocarbon could also be added to the inspiratory gases in a breathing circuit at any point away from the face. Mist could be administered to spontaneously breathings lungs or mechanically ventilated lungs.

The perfluorocarbon mist extracts heat from the lungs in three distinct stages: (1) depending on the specific heat of the liquid perfluorocarbon, heat is extracted from the lungs to the point of vaporization; (2) depending on the latent of vaporization, more heat is extracted for the perfluorocarbon to change from liquid phase to gaseous phase; and finally (3) depending on the specific heat of the perfluorocarbon vapor, further heat is extracted to warm the vapors to body temperature. A small amount of heat transfer occurs from the tracheobronchial tree to the perfluorocarbon droplets by radiation and conductive heat transfer by immediate contact with the tracheobronchial tree wall.

Our theoretical and laboratory data shows a 5–10 fold increase in the heat transfer rate even when small amount of perfluorocarbon mist is added to cooled helium-oxygen mixture. In one experimental protocol using 1% perfluorocarbon mist added to 80% helium and 20% oxygen mixture cooled to 0° C, pigs cooled at a rate of approximately 12° C. per hour. The rate of cooling increased in proportion to increased volume concentration of perfluorocarbon mist.

FIG. 7 is a graph of a theoretical cooling rate for a 70 kg. adult male breathing normally. The adult is breathing Heliox with varying percentages of PFC FC 87 mist. The X axis is the volume/volume percentage ratio of liquid PFC to Heliox. The Y axis is the cooling rate. For example, at 1%, there is 1 cc of liquid PFC that has been atomized and injected into 100 cc of Heliox. At 1%, the theoretical cooling rate is about 12 degrees centigrade per hour.

Use Medications to Suppress Reflex Rewarming

When the temperature of the blood perfusing the brain is lower than normal 37° C., temperature sensitive neurons in the hypothalamic thermoregulatory center of the brain trigger mechanisms in the body to produce heat. This reflex heat production occurs predominantly in the skeletal muscles, solid organs and brown fat. In the skeletal muscles shivering occurs to generate heat. In the solid organs and adipose tissue, metabolism is increased in response to secreted hormones such as epinephrine, norepinephrine, cortisol and thyroxine. In order to achieve mild to moderate hypothermia, the authors recommend that this reflex heat production by the body be suppressed or eliminated.

The central hypothalamic thermoregulatory center is sensitive to a wide variety of nervous system depressants. These agents include general anesthetics, narcotics, and sedatives. An ideal agent would be a narcotic such as morphine, demerol, or fentanyl. Drugs that act on serotonin and dopamine receptors may also be administered to act on the thermoregulatory center.

Peripheral heat production in the skeletal muscles can be blocked by neuromuscular blocking agents such as curare, pancuronium, and succinylcholine. When these agents are used, spontaneous respirations will be abolished and the healthcare practitioner must be able to maintain artificial respiration of the subject. Agents that act at the level of the spinal cord, such as demerol, clonidine, and nefopam, may also be used to prevent activation of spinal neurons responsible for shivering.

Heat production in solid organs and adipose tissues is primarily dependent on the effect of hormones secreted in response to hypothermia. These hormones include thyroid-stimulating hormone (TSH), thyroxine, catecholamines, and coticosteroids. Short-term hypothermia, lasting several hours to a few days may be enhanced by use of anti-catecholamine drugs such as reserpine, clonidine and propranolol. Anti-thyroid agents may be considered for prolonged hypothermia lasting several days. The practitioner should take into account the overall clinical status of the subject and the side effects of these drugs when they are administered to induce hypothermia.

Endotracheal Tubes and Other Hardware

The present invention includes insulated endotracheal tubes. Insulated endotracheal tubes of different sizes can be used for administration of cooled or heated heliox, mixed with or without atomized PFC. The present invention also includes insulated endotracheal tubes with an adopter for a PFC injector. In this version, the insulated endotracheal tube is attached to a universal adopter that permits the introduction of an injector or a needle shaped device or atomizer for atomization of PFC within the endotracheal tube or projecting outside of the tip of the endotracheal tube. One insulated endotracheal tube includes an adopter having a PFC injector and a Heliox introducer tube. The PFC and Heliox may be delivered into the endotracheal tube as a single unit, comprised of a PFC tube within a Heliox tube. Alternatively, the PFC and the Heliox may be delivered in two separate tubes into the endotracheal tube. In this version, the insulated endotracheal tube can be attached to a universal adopter with a port or ports that permit the introduction of the PFC and Heliox tubes. The present invention includes delivery tubes for the PFC and Heliox. The PFC and Heliox may be delivered to the endotracheal tube in an insulated tube for the Heliox, with another tube inside this said tube for the PFC. The PFC and Heliox may be also be delivered in separate insulated or non-insulated tubes.

The present invention also includes devices to cool the Heliox and PFC. Any method know to experts in the art of refrigeration may be used to cool the heliox and PFC, prior to delivery into the lungs. Any device or method known in the art may be used to recapture the moisture emanating from the lungs. Any device or method known in the art may be used to condense the expired PFC vapors. Any device or method known in the art may be used to absorb the expired carbon dioxide. A pump or compressor or any other device known in the art may be used to maintain the flow rate and pressure in the breathing system. Thermometers to monitor temperature of the inspired gases, expired gases, PFC, Heliox and body temperature can be used. Any device or method known in the art may be used to monitor the temperatures. The concentration of oxygen, helium, nitrogen, and carbon dioxide can be monitored in the inspired and expired gases using any device known in-the art. The concentration of PFC mist and vapor in the inspired and expired gases can be measured using any device known in the art. The pressure and flow of gases and mist and vapor in the inspiratory and expiratory limbs of the breathing circuit can be measured using any device known in the art. A permanent or disposable container that holds a known amount of PFC for the purpose of atomization can also be used. The device may also be used for storage of the recaptured PFC from the expiratory limb of the breathing circuit.

Ventilators

A ventilator is a device used to move gas into the lungs. The design of the ventilator may be such that lung inflation is accomplished by (1) applying subatmospheric pressure around the chest, or (2) by applying positive pressure directly to the airway. The positive pressure ventilators are the most commonly used ventilators. (Ventilators: theory and clinical application. Dupuis, Yvon G. The C. V. Mosby Company, St. Louis, Mo. 1986). The power source required to operate the ventilator is provided by either compressed air (pneumatic ventilators), electricity, or both (electronic ventilators).

The gases moved into the lungs may include air, oxygen, nitrogen, carbon dioxide, helium, nitrous oxide, anesthetic vapors and other inert gases. The gases may be pumped into the ventilator from (a) wall outlets in the hospital; or (b) gas cylinders attached to the ventilator. In pneumatic ventilators, either oxygen or air may be used as the driving gas to move other gases into the lungs.

There are several control parameters on the ventilator that determines how respiratory gases are administered into the lungs. This includes (1) respiratory rate, (2) the tidal volume, (3) mode of triggering inspiration, (4) mode of termination of inspiration—pressure limited, or volume limited, (4) inspiration: expiration duration—I:E ratio, (5) inspiratory flow rate, and (6) positive end expiratory pressure—PEEP.

The respiratory gases pumped out of the ventilator enter the breathing circuit. The inspiratory limb of the breathing circuit carries the gases to the patient's lungs. The expired gases from the lungs are carried back to the ventilator in the expiratory limb of the breathing circuit. The expired gases may be completely vented into the scavenging system (open circuit) or re-breathed by the patient, after absorption of the carbon dioxide (closed circuit).

Breathing Circuits

The breathing circuit refers to the system of tubings that connect the patient to the anesthesia machine or the ventilator. They carry gases from the ventilator to the patient and return the expired gases back to the ventilator. For example, a typical breathing circuit may be composed of: (1) an inspiratory conduit that delivers fresh gases to the patient; (2) an expiratory conduit, that delivers expired gases from the patient to the ventilator; (3) a face mask, endotracheal tube, or other suitable upper airway device to deliver gases in and out of the lungs; and (4) a Y-connector to connect the inspiratory and expiratory conduits to the upper airway device. In some forms of breathing circuits, a spring loaded positive pressure release valve and a collapsible reservoir bag, may be added to the expiratory conduit.

Often, the inspiratory and expiratory conduits are made of disposable corrugated plastic or rubber tubings. The upper airway device such as the face mask and endotracheal tube and the Y-connector are also made of biocompatible disposable plastic or rubber material. The breathing circuit may contain ports for sampling gases, to measure the temperature, add humidity and administer aerosolized drugs.

Anesthesia Machines

Anesthesia machines are devices that safely administer anesthetic vapors and gases. An anesthesia machine can have a source for gases, vaporizer for anesthetic agents, ventilator, breathing circuit, carbon dioxide absorption device, monitors and controls. The gases used in the anesthesia machine may include, air, oxygen, nitrogen, nitrous oxide, carbon dioxide, or inert gases. The gases may be pumped into the machine from wall outlets or attached gas cylinders. Flow meters, pressure gauges and gas sensors are used to measure the quantity and quality of gases that flow into the breathing circuit. The vaporizers are agent specific and add set concentration of anesthetic vapor to the respiratory gases. The ventilator is used to mechanically move gases into the lungs using positive airway pressure. Soda lime or baralyme granules are the common agents used to absorb the expired carbon dioxide. Safety monitors can be set to alarm when the gas pressure, gas flow, concentration of oxygen, concentration of carbon dioxide, or the anesthetic vapor pressure are either high or low over a set range of values. Examples of Anesthesia Machines include: (1) Narkomed 4 Anesthesia System—manufactured by North American Drager, Telford, Pa. And (2) Ohmeda CD Anesthesia System—manufactured by Ohmeda, BOC Health Care, Inc., Madison, Wis.

Partial Liquid Ventilation (PLV)

Hypothermia may be achieved with Partial Liquid Ventilation using cooled perfluorocarbon (PFC) and cooled heliox. Applicants believe that the addition of small amounts of perfluorocarbon into the tracheobronchial tree helps to break the temperature barrier that exists between the upper airways and the distal airways. Distal airways once flooded with perfluorocarbons tend to conduct heat more uniformly to the blood in the alveolar sacs than gases. Perfluorcarbons decrease the surface tension and thereby open up normally collapsed alveoli. This recruitment effect of PFC adds more alveoli to the heat exchange process, which were otherwise unavailable. Since the thermal capacity of the liquid PFC is far greater than air or heliox, applicants believe that the quantity of heat transferred to or from the alveolar blood is greater with liquid ventilation. The evaporative heat loss from the lungs due to the vaporization of the PFC further adds to the cooling effect.

Cooled, liquid perfluorocarbon can be administered into the lungs through the endotracheal tube. The perfluorocarbon may be pre-oxygenated and cooled to 0–4° C. and poured into the endotracheal tube in small aliquots of 1 ml/kg body weight. The dose can be injected into the endotracheal tube through an adopter with a side injection port. The injection can be done slowly over a period of 5–10 minutes. During the administration, mechanical ventilation can be continued with cooled heliox. The dosing of PFC can be stopped once: (1) a total dose of 5 ml/kg has been reached within an hour; or (2) a total dose equivalent to predicted Functional Residual Capacity has been administered; or (3) a meniscus is visible at the proximal end of the endotracheal tube at the end of an expiration, without any positive end expiratory pressure applied to the endotracheal tube.

Mechanical ventilation with cooled heliox can be continued during and after the instillation of PFC into the lungs. The inspired heliox can be cooled to 0-4° C. The mode of mechanical ventilation with heliox may be any form of conventional ventilation, either pressure-limited, volume-limited, oscillatory, pulsatile or jet ventilation. Arterial blood gases, blood acid-base balance and hemodynamic stability preferably determine the parameters of the mechanical ventilation. For example, in the volume controlled ventilation mode, the ventilator tidal volume could be 5–10 ml/kg, respiratory rate 10–14 breaths/minute, positive end expiratory pressure of 5 cm H2O, and inspired oxygen concentration of 30% and helium70%. The ventilator parameters may be adjusted to keep the PaO2 values greater than 55 mm Hg and PaCO2 values less than 55 mm Hg. Any other form of clinically acceptable gas mechanical ventilation may be used to ventilate the partially PFC filled lungs with heliox.

Total liquid ventilation (TLV) may also be used to change body temperature. Liquid perfluorocarbon can be introduced into the lungs, and total liquid ventilation performed using Heliox instead of air. The cooled or warmed perfluorocarbon may benefit from having the heat transfer properties of Helium included in the liquid solution in the lungs.

Forced Air Cooling Blankets

The cooled, Heliox gas mixture can be combined with a forced air cooling blanket to even more rapidly reduce the temperature of a patient. Once the target temperature is reached, hypothermia may be maintained using heliox alone or in association with other adjunctive hypothermia procedures. Applicants believe that the addition of forced air surface cooling, using specialized cooling blankets can dramatically hasten the process of hypothermia. In large animals, the addition of forced air surface cooling, using a forced air cooling blanket, appears to hasten the onset of hypothermia.

Illustrated Embodiments of the Invention

FIG. 1 illustrates a system 20 for heating and/or cooling oxygen carrying gas administered to a patient to heat and/or cool that patient through the lungs. System 20 includes a gas mixing conduit or chamber 22, a cooling and/or heating device 24, and a ventilator 28. As used in this example, cooling/heating device 24 represents cooling only devices, heating only devices, and devices that can be used to both cool and heat gas, in different modes. System 20 can include or be coupled to an oxygen gas tank or source 32 through an oxygen safety interlock 34 and include or be coupled to an oxygen flow meter 36 that feeds mixing chamber 22. System 20 can also include or be coupled to a helium gas tank or source 38 through a helium safety interlock 40 and include or be coupled to a helium flow meter 42 that feeds mixing chamber 22. The safety interlocks 34 and 40 are well known to those skilled in the art, can be pin index systems, and are used to insure that conduits or tubes intended to be connected to a specific gas are mechanically able to be connected only to that type of gas, and no other.

The Pin Index Safety system was developed in the 1950's to prevent the attachment of the wrong gas cylinder to the yoke on an anesthesia machine. Attaching the wrong gas cylinder could result in the administration of hypoxic gas mixture, i.e., one that contains less than 21% oxygen, to the patient. The Pin Index Safety system consists of two pins projecting from the anesthesia machine's cylinder yoke, which correspond to two holes drilled into the cylinder valves on the gas cylinder. The precise location of the pins on the yoke and the complementary holes in cylinder valve are specific for each gas. This ensures that a yoke containing pins will accept only the correct cylinder valve. Thus, as used herein, a hose adapted to couple specifically to a certain gas includes reference to such a pin index system.

Mixing chamber 22 can be coupled to a one-way valve 23 that is coupled to an inlet port 44 in heater/cooler 24. Heater/cooler 24 can include heating/cooling coils 25 in some embodiments. Any suitable device for heating or cooling the oxygen carrying gas can be used. Heating/cooling device 24 includes an outlet port 46 that is coupled to a heating/cooling device outlet conduit 48. Outlet conduit 48 is coupled to an inspiratory limb 50 that is coupled to a Y or T-connector 52 that is coupled to an endotracheal tube 26 inserted within a trachea 56 leading to lungs 54. T-connector 52 is also connected to an expiratory limb 58 that is coupled to ventilator 28. Ventilator 28 can be any suitable ventilator, well known to those skilled in the art. Ventilator 28 can be attached to any suitable portion of the tubing coupled to the lungs. In some embodiments, the ventilator is combined with the cooling/heating device. In some embodiments, the cooling/heating device is located upstream of the cooling heating device, such that the gas is cooled or heated gas after being passed through the ventilator. Respired gas from the system can pass through a scavenger system at 60, for capturing substances, including anesthesia gases and any perfluorocarbons, as later described. The outlet gases at 60 can also be recirculated back to ultimately feed the inspiratory limb in some embodiments, after scrubbing and adding new gases, a concept that is well known to those skilled in the art. Respiratory bag 30 acts as a reservoir for respiratory gases, provides visual assessment of respiration, and serves as means to provide manual ventilation.

Figure 2:
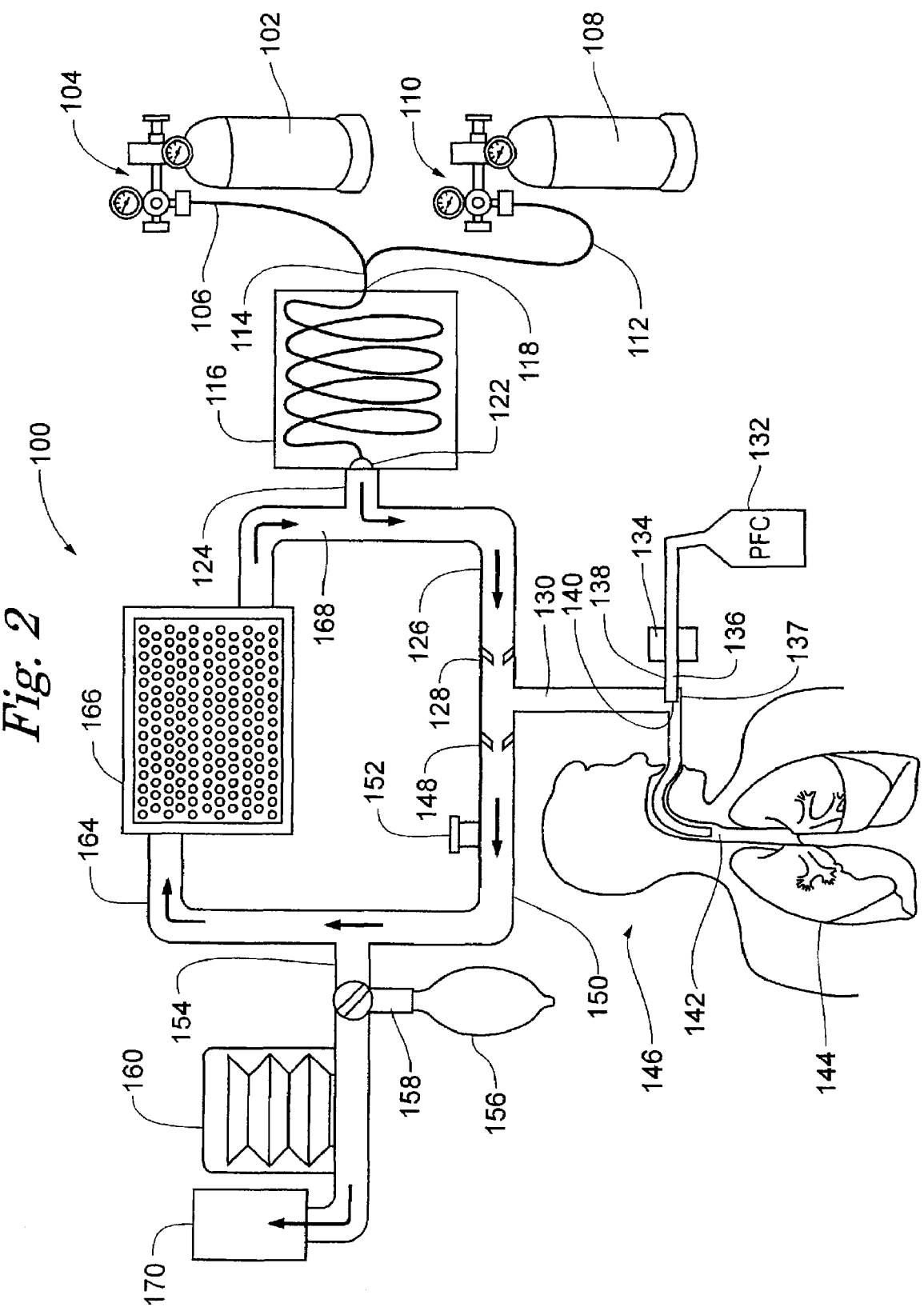
FIG. 2 is a schematic representation of a cooling system having helium and oxygen coupled to a refrigeration chamber providing cooled gases to an insulated breathing circuit coupled to a patient's lungs through an endotracheal tube, having a carbon dioxide absorber or scrubber, and coupled to a scavenging system.

FIG. 2 illustrates another system 100 for cooling a human patient 146 through the patient's lungs144. System 100 includes an oxygen source 102 coupled through an oxygen safety interlock 104 through an oxygen tube or hose 106 to a mixing chamber or conduit 114. System 100 also includes a helium source 108 coupled through a helium safety interlock 110 through a helium tube or hose 112 to mixing chamber or conduit 114. Mixing chamber or conduit 114 is coupled a cooler 116 through a cooler input port 118. The helium-oxygen gas can flow through and be cooled by cooler 116, exiting through a cooler outlet port 122. Cooler 116 can be any suitable gas cooling device that can cool the mixed gas to the desired low temperature. In some systems, cooler 116 is coupled through a control system or controller to control the degree of cooling provided by the cooler. In one system, a temperature sensor is located downstream of the cooler, for example, near the distal region of an endotracheal tube. The temperature sensor can be coupled as an input to the controller, that can act as a feedback controller to control cooler 116. In this way, the temperature of the gas mixture as delivered to the patient's trachea can be controlled to a desired set point.

Cooler 116 can have an outlet port 122 that is coupled to an outlet conduit 124 that feeds an inspiratory limb 126 in the embodiment shown. The gas mixture can pass through an inspiratory one-way valve 128 and into a T-connector 130 then into an endotracheal tube 142. In embodiments of the invention using atomized liquid, a liquid source 132 can be coupled through a liquid cooler 134 and to a cooled liquid outlet conduit 136 that discharges directly or indirectly into endotracheal tube 142. In one embodiment, cooled liquid outlet tube 136 has a distal end 140 that acts as an atomizer to produce liquid droplets that can be carried with the helium-oxygen gas into the lungs. In some embodiments, the point of liquid atomization is located well inside the trachea, and can be located within the endotracheal tube. An adopter or adapter 137 can be seen coupled to the proximal end of endotracheal tube 142. Adopter 137 can be an elbow shaped tube that is coupled at one end to the external gas source and at the other end to the endotracheal tube. Adopter 137 can include a side port or nipple for admitting an atomized liquid or a tube carrying the liquid to be atomized.

The expired gas can be respired through an expiratory one-way valve 148 and through expiratory limb 150. A pop-off valve 152 can be included in expiratory limb 150. Expired gas can continue through a CO2 scrubber inlet conduit 164, through a CO2 scrubber 166, then through a CO2 scrubber outlet conduit 168. The expired gases can also be coupled to conduits 154 and 158 to a respiratory bag 156. The respiratory bag 156 acts as a reservoir for respiratory gases, provides visual assessment of respiration, and serves as means to provide manual ventilation. A ventilator 160 may be seen coupled to conduit 154 and can provide positive pressure ventilation to patient 146. Ventilator 160 can be a ventilator suitable for handling the cooled, helium-oxygen mixture. Gases can be passed through a scavenger system 170 that can include condensers for recovering any liquid that was atomized and is to be recovered. Scavenger system 170 can be used to recover perfluorocarbons, where used.

Figure 3:
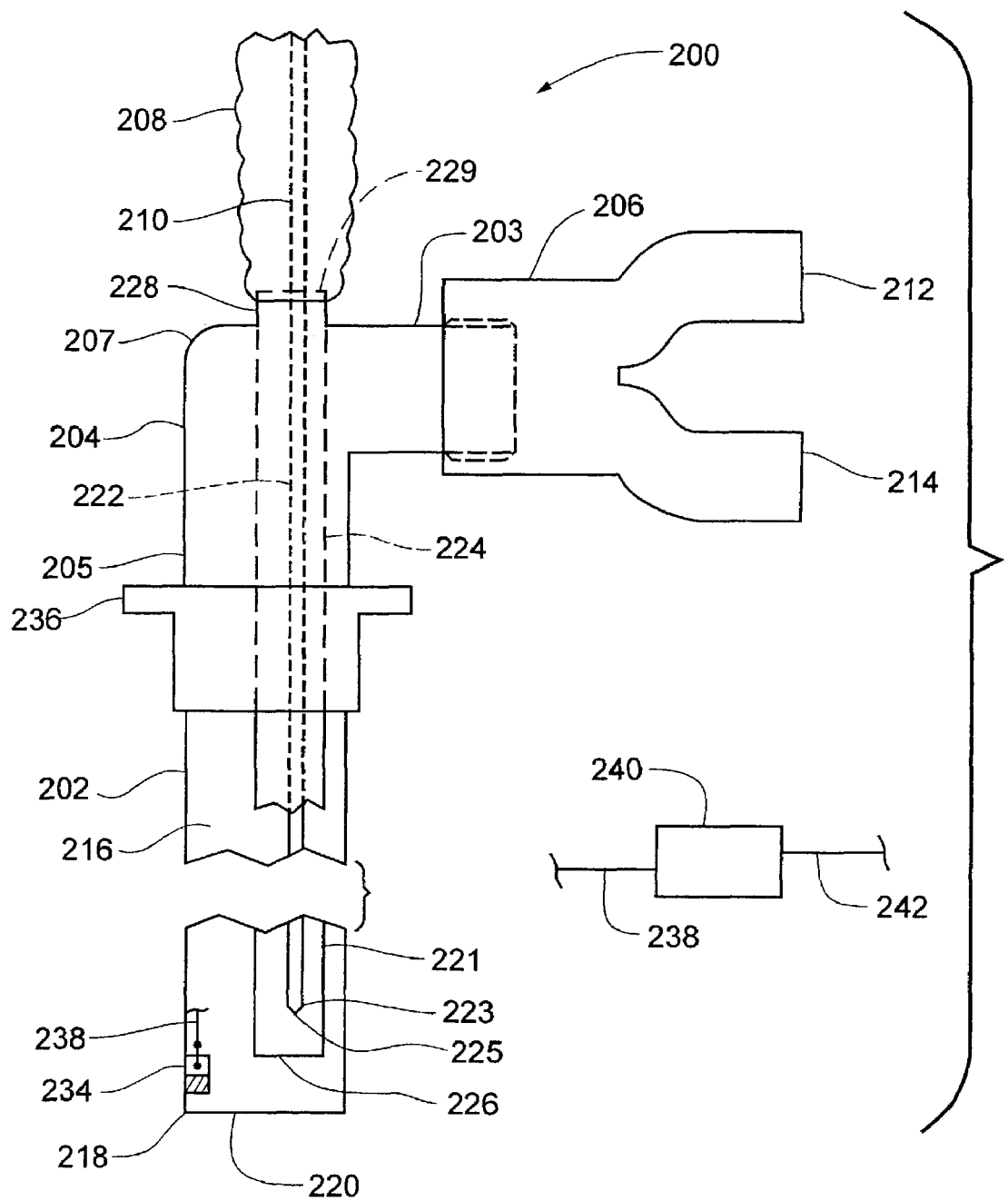
FIG. 3 is a longitudinal, cross-sectional view of an insulated, ventilation tube coupled to an adopter and perfluorocarbon injection tube.

FIG. 3 illustrates a system 200 that can be used to administer a Heliox gas alone, or a Heliox gas carrying atomized liquids, for example, perfluorocarbons. System 200 includes a Heliox supply tube 208 having a liquid supply tube 210 that can be used to deliver a liquid perfluorocarbon. Heliox supply tube 208 is coupled to an adopter or adapter 204 through a port 229 in a nipple 228 that has an inside diameter. Adopter 204 includes a first region 203 coupled to a splitter or Y-connector 206 having an inspiratory coupling 212 and expiratory coupling 214. First region 203 is coupled through a bend 207 that curves around to a second region 205 that has a second region inside diameter. Adopter second region 205 is coupled to a connector 236 disposed at the proximal end of an endotracheal tube 202. Endotracheal tube 202 has a lumen 216 within and extends to a distal region 218 having a distal port 220. Endotracheal tube 202 can have an insulated wall so as to have at least twice the insulating value of an endotracheal tube having only a ⅛th inch thick silicone rubber or polyurethane wall. Endotracheal tube 202 preferably has an inflatable distal cuff as is found on most endotracheal tubes (not shown in FIG. 3 to simplify the drawing.) In some embodiments, endotracheal tube 202 includes a temperature sensor 234 coupled to an electrode or wire 238 that can be coupled to a temperature controller 240 that can control a cooling or heating device through a controller output wire 242.

A heliox delivery tube 224 is disposed within endotracheal tube 202, and extends to a distal region 221 and has a distal port 226. Heliox delivery tube 224 can have a liquid delivery tube 222 disposed within, extending to a distal region 223 and distal port 225. In some embodiments, distal port 225 has the proper diameter and is located at the proper distance from heliox delivery tube distal port 226 or port 220 so as to function as an atomizer.

In some embodiments, nipple port 229 has an inside diameter that is at least about ⅓, or ½ the inside diameter of adopter inside diameter region 205, depending on the embodiment. Adopter 204 can have port 229 and nipple 228 aligned with adopter second region 205 so as to allow tubes such as liquid tube 222 and heliox tube 224 to enter second region 205 and further enter endotracheal tube 202. In some embodiments, a separate liquid delivery tube is not present within endotracheal tube 202, and even within adopter 204. In these embodiments, heliox tube 208 may carry an atomized liquid.

Figure 4:
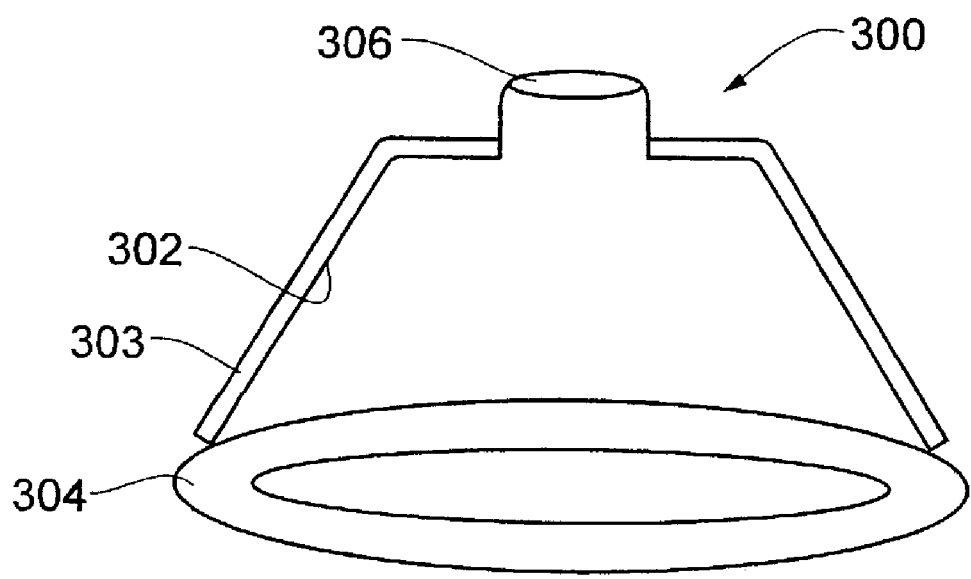
FIG. 4 is a highly diagrammatic, cut-away view of an insulated face mask.

FIG. 4 illustrates an insulated mask 300 that can be used as part of the present invention. Mask 300 can be used to particular advantage in sports related overheating situations and in ambulances by first responders to treat ischemic events or other events. Mask 300 includes a mask wall 302 and can include an insulation layer 303 that is insulated relative to mask walls of masks formed of silicone rubber or polyurethane. Some embodiments have an insulating value at least twice that of a silicone rubber or polyurethane mask having a wall thickness of ⅛ inch or 3/16 inch, depending on the embodiment. Mask 300 can also include a port 306 and an inflatable cuff or face seal 304.

Experimental Data

Figure 5:
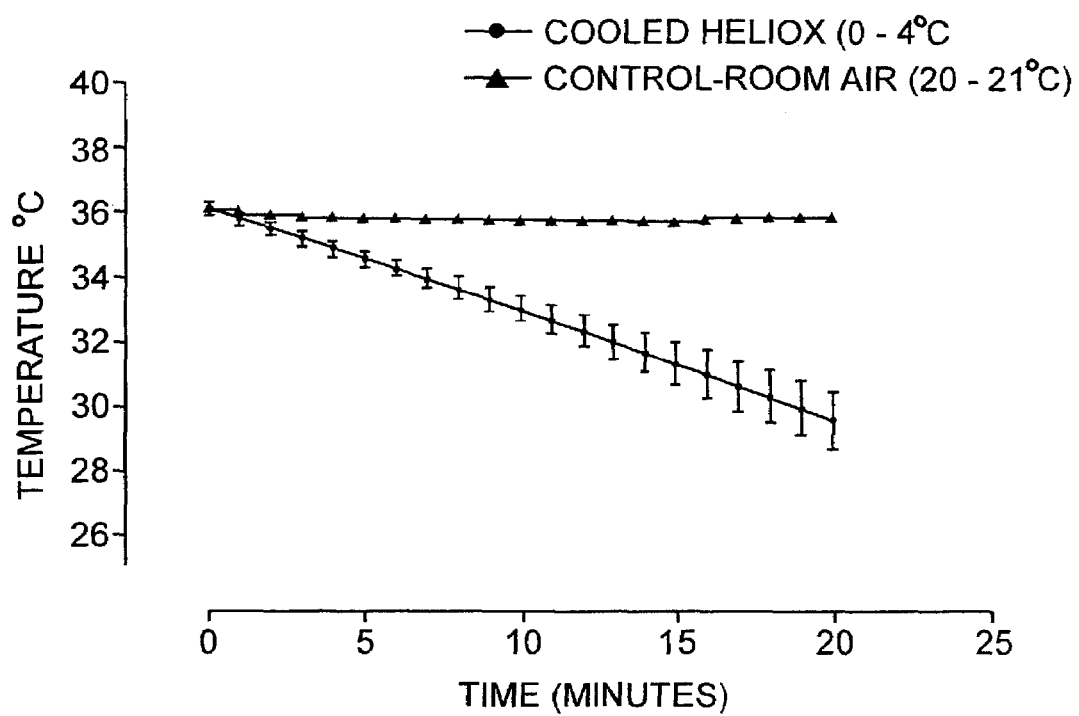
FIG. 5 is a graph showing cooling of brain temperature with institution of described methodology.

Twelve male Sprague Dawley rats weighing 440±5 g were equally divided into study and control groups. All animals were anesthetized with intraperitoneal injection of 50 mg/kg of ketamine and 25 μg/kg of fentanyl. The animals were intubated through a tracheotomy with a 14-gauge angiocatheter. One of the femoral arteries was cannulated with 24-gauge angiocatheter for blood pressure and blood gases measurements. Using room air, both groups of animals were ventilated with a tidal volume of 5–6 ml/kg, at a respiratory rate of 30 breaths/minute. At this minute ventilation, arterial carbon dioxide tension (Paco2) was maintained in the normal range. The animals were turned prone and brain ventriculostomy was performed through a left parietal burr hole. A thermister probe was introduced into the lateral ventricle and sealed in place with bone wax. Another thermister probe was introduced into the colon through the rectum. The ventilatory gas of the study group was switched to a 1:4 mixture of oxygen and helium, cooled to 4° C. The respiratory rate of both groups was increased to 60 breaths/ minute. The brain and rectal temperatures were recorded every minute for 20 minutes. The blood gases were checked at the end of 20 minutes. In both groups the drop Paco2 were similar; however, the drop in brain temperature was significant in the study group. The brain temperature dropped at a rate of 0.3±0.08° C. per minute in the experimental group. There was no significant drop in the temperature of the control group. The results of the brain cooling are shown in the graph in FIG. 5.

Human Experiment Using Cooled Heliox

Adult male volunteers were allowed to breath through a face-mask, a cooled (−10 to 4° C.) mixture of 21% oxygen and 79% helium, for several hours at 10 L/minute. This lowered their tympanic membrane temperature at a rate of 0.05–0.07° C. per minute. During the study the room temperature was kept 68–72° F. Our calculations suggest that addition of 1% FC-87 perfluorocarbon mist would have increased the rate of cooling 2–3 fold. Use of drugs and an insulated or double-walled endotracheal tube is expected to increase the rate of cooling as well.

Some Exemplary Uses for the Described Method of Hypothermia

Applicants believe that the described method of hypothermia can be used to prevent or retard the process of cell death in various organs following ischemia. The widest applications would be in the realm of cardiac, brain, spine and organ transplant surgeries, where there is a potential for ischemia. Injury can be minimized and recovery hastened when hypothermia is instituted early following heart attacks and strokes. It may be used to control intracranial hypertension from a wide variety of causes, including head injury, strokes, surgery, neoplasms and poisons. The method would also be effective in lowering the body temperature, especially in children following infections. The simplicity and rapidity of cooling would render this method effective in the management of malignant hyperthermia, an otherwise often fatal condition. Hypothermia, by retarding cellular metabolic process, may also find use in prolonged space travel and retardation of aging process in certain species.

Exemplary Uses for the Described Method of Warming

The described method would be effective in rewarming the body following any form of therapeutically induced hypothermia. It is also a safe and effective method to rewarm the body following accidental hypothermia caused by such incidents as drowning and exposure. The described method is ideally suited to maintain normal body temperature during prolonged general anesthesia and rewarming after prolonged operations. Premature infants, neonates and fragile malnourished adults who have difficulty maintaining body temperature may also benefit from inhaling warmed heliox circulated inside a gas tent or plastic hood. Warming the body is believed by some to reduce the viral load in the bloodstream. Warming the body is believed by some to be a tool useful in treating viral diseases, Hepatitis-C, and even AIDS. The present invention can be used to warm the body to temperatures of over 102, 103, 104, 105, or 106 degrees Fahrenheit, to treat viral disease:

Exemplary Applications for the Described Method of Hypothermia and Warming

In all of the following exemplary applications, perfluorocarbon mist or vapor may be added to the cooled or warm heliox, respectively. Perfluorocarbon mist added to the cooled heliox would accelerate the cooling process and the perfluorocarbon vapors added to warmed heliox would accelerate the warming process.

In the field: Portable units of cooled heliox may be taken to the field by paramedics and administered to the patient by either using a face mask or an endotracheal tube. Following an ischemic episode, since time is of the essence, initiating hypothermia in the field would be an early start in retarding cell death. Warmed heliox at the site of accidental hypothermia would be effective in early reversal of the condition.

In the ambulance: Portable ventilators can be set up to administer cooled or warmed heliox in the ambulances so as not to loose valuable post-ischemic time.

In the emergency rooms: In emergency rooms patients can be maintained hypothermic or warm, until they are triaged to appropriate sections of the hospital. Regular ventilators or portable ventilators designed to administer cooled or warm heliox would serve this purpose well.

In the operating rooms: Anesthesia machines equipped to deliver cooled or warmed heliox may be used to induce hypothermia or warm the patient during surgery.

In the intensive care units: Ventilators designed to deliver cooled or warmed heliox would find predominant use in the intensive care units. Profound hypothermia or warming could be effectively induced and maintained following endotracheal incubation and mechanical ventilation.

In the hospital wards: Mild to moderate hypothermia may be maintained by non-invasive ventilation, such as nasal BiPAP, using cooled heliox on patients in hospital wards. Warmed heliox may be used to maintain body temperature in patients who require ventilatory assistance.

Miscellaneous applications: Pneumatic bubbles circulating cooled or warmed heliox may be used to warm or cool the body during space travel, to warm or cool new born babies.

Applicants believe that the effects of combining helium and perfluorocarbon in the inspired gas mixture of the present invention may be more than a mere mechanical conduit for heat transfer. The combination of heliox and perfluorocarbon might have pharmacological and physiological effects on the body that translates into hypothermia more profound than what can be accounted for by mere physical law of heat transfer. The combination of heliox and perfluorocarbon may possess pharmacological and physiological effects that hasten the onset of hypothermia to greater degree than that is possible by mere mechanical scavenging of heat from the lungs.

What is claimed is:

1. A method for medical treatment comprising:
    selecting a human patient that has had an ischemic event or is undergoing a surgery associated with a significant probability of causing ischemia;
    providing a cooled gas mixture comprising helium and oxygen and having a temperature of less than about, 10 degrees Centigrade; and
    ventilating the patient using the cooled gas mixture to lower the patient's core body temperature to reduce tissue oxygen consumption,
    wherein the method further comprises providing a liquid having a boiling point of less than 37 degrees Centigrade, atomizing the liquid into droplets, and wherein the ventilating step includes ventilating the patient with the gas mixture, with the gas mixture forming a substantially continuous phase and the liquid droplets being carried in the gas mixture.

2. A method as in claim 1, wherein the cooled gas mixture has a temperature of less than 5 degrees Centigrade.

3. A method as in claim 1, wherein the selecting step includes selecting a patient that has had an ischemic event selected from the group consisting of heart attacks and strokes.

4. A method as in claim 1 wherein the providing liquid provides a perfluorocarbon.

5. A method as in claim 4, wherein the providing liquid provides a perfluorocarbon having oxygen solubility sufficiently high to sustain life for at least a one hour procedure.

6. A method as in claim 4, wherein the perfluorocarbon includes perfluorocarbons having the formula C5F12.

7. A method as in claim 1, wherein the ventilating includes injecting the atomized liquid into the gas mixture outside of the patient.

8. A method as in claim 1, wherein the ventilating includes injecting the atomized liquid into the gas mixture inside of the patient's trachea.

9. A method as in claim 1, wherein the perfluorocarbon liquid forms a substantially continuous liquid phase having at least some of the gas mixture dissolved within.

10. A method as in claim 1, wherein the perfluorocarbon liquid forms a substantially continuous liquid phase having at least some of the gas mixture comprising bubbles entrained within.

11. A method as in claim 1, wherein the gas mixture comprises at least 50% helium by volume.

12. A method as in claim 1, wherein the method further comprises administering at least one drug that suppresses reflex heat production by the human being body when cooling occurs.

13. A method as in claim 1, wherein drugs are administered to the patient to enhance and/or maintain hypothermia, wherein the drugs are selected from the group consisting of general anesthetics, narcotics, sedatives, morphine, Demerol, fentanyl, drugs that act on seratonin and/or dopamine receptors, neuromuscular blocking agents, curare, pancuronium, succinylcholine, clonidine, nefopam, anti-catecholamine drugs, reserpine, propranolol, and anti-thyroid agents and combinations thereof.

14. A method as in claim 1, wherein the ventilating step includes supplying the cooled gas mixture through an insulated tube to an endotracheal tube or face mask.

* * * * *